(12) United States Patent
Vitullo et al.

(10) Patent No.: US 7,976,506 B2
(45) Date of Patent: Jul. 12, 2011

(54) SYRINGE WITH SELECTABLE INDICIA OF CONTENTS

(75) Inventors: Jeffrey M. Vitullo, Pottstown, PA (US); Matthew J. Moore, Ephrata, PA (US); Richard L. Harding, Reinholds, PA (US)

(73) Assignee: Arrow International, Inc., Reading, PA (US)

( * ) Notice: Subject to any disclaimer, the term of this patent is extended or adjusted under 35 U.S.C. 154(b) by 1258 days.

(21) Appl. No.: 11/541,280

(22) Filed: Sep. 29, 2006

(65) Prior Publication Data

US 2008/0171995 A1    Jul. 17, 2008

(51) Int. Cl.
*A61M 5/00* (2006.01)
(52) U.S. Cl. ...................................... 604/187
(58) Field of Classification Search ............... 604/47.03, 604/100.01, 404, 110, 111, 187, 186, 189, 604/68, 198, 192, 220, 227, 232
See application file for complete search history.

(56) References Cited

U.S. PATENT DOCUMENTS

| 2,283,915 | A | | 5/1942 | Cole |
| 3,232,117 | A | | 2/1966 | Gilmont |
| 3,391,694 | A | | 7/1968 | Spaeth |
| 3,815,785 | A | | 6/1974 | Gilmont |
| 3,885,562 | A | * | 5/1975 | Lampkin ................ 604/189 |
| 4,056,096 | A | | 11/1977 | Collica et al. |
| 4,178,071 | A | | 12/1979 | Asbell |
| 4,743,234 | A | | 5/1988 | Leopoldi et al. |
| 5,489,275 | A | * | 2/1996 | Thompson et al. ........... 604/264 |
| 5,498,243 | A | | 3/1996 | Vallelunga et al. |
| 6,042,562 | A | | 3/2000 | Armor |
| 6,120,481 | A | | 9/2000 | Rennert et al. |
| 6,315,760 | B1 | | 11/2001 | Sharp |
| 6,338,200 | B1 | | 1/2002 | Baxa et al. |
| 6,420,657 | B1 | | 7/2002 | Fang et al. |
| 6,699,223 | B2 | | 3/2004 | Sharp |
| 6,821,266 | B2 | * | 11/2004 | Knepshield et al. ........... 604/110 |
| 2003/0050609 | A1 | | 3/2003 | Sams |
| 2004/0186437 | A1 | | 9/2004 | Frenette et al. |

OTHER PUBLICATIONS

PCT/US07/079703SR, Sep. 27, 2007, Arrow International, Inc.
PCT/US07/079703WO, Sep. 27, 2007, Arrow International, Inc.

* cited by examiner

*Primary Examiner* — Nicholas D Lucchesi
*Assistant Examiner* — Christopher D Koharski
(74) *Attorney, Agent, or Firm* — Baker & Hostetler LLP (57) ABSTRACT

A syringe includes a barrel defining a liquid chamber, an aperture and two or more contents indicators; a plunger movable within said barrel whereby movement of the plunger in a first direction causes the liquid chamber to fill with a fluid and movement by the plunger in a second direction causes fluid to be expelled from the liquid chamber through the aperture; and a selecting mechanism disposed on the barrel that is actuated to select only one of the contents indicators.

24 Claims, 13 Drawing Sheets

SYRINGE WITH SELECTABLE INDICIA OF CONTENTS

FIELD OF INVENTION

This invention relates to syringes and more particularly to syringes provided with selectable indicia of contents.

BACKGROUND OF THE INVENTION

Syringes are used in various medical procedures for introducing fluids into vessels, cavities or medical devices, e.g. catheters or other access devices. Virtually any liquid can be introduced via a syringe, including a large selection of liquids introduced into a patient for therapeutic purposes, e.g. liquid medications.

Once a liquid is contained within the barrel of a syringe, it can be difficult to determine accurately and quickly the identity of the liquid. Many liquids introduced via syringe are weak solutions containing primarily water, and are thus visually indistinguishable from each other. In addition, it is usually of critical importance to know what liquid is being introduced and to avoid the introduction of other liquids. The amount of a particular liquid to be introduced is also usually critical. The possibility of confusion coupled with the adverse consequences that could result for the administration of the wrong medicine requires the proper identification of a fluid to be introduced into a patient.

U.S. Patent Application Publication No. 2004/0186437 discloses a syringe structure for identifying the contents of the syringe by printing on the barrel or plunger of the syringe. Similarly, U.S. Pat. No. 6,315,760 discloses a coating applied to the outer surface of the syringe barrel, where the coating may be inscribed with contents identification using a pen or marker.

Accordingly, there is a need for simple, convenient, inexpensive structure and method of identifying the contents of a syringe without having to choose a particular barrel or plunger beforehand or requiring the recording of contents using a pen.

SUMMARY OF THE INVENTION

A syringe according to an exemplary embodiment of the invention includes a barrel defining a liquid chamber, an aperture and two or more contents indicators; a plunger movable within said barrel whereby movement of the plunger in a first direction causes the liquid chamber to fill with a fluid and movement by the plunger in a second direction causes fluid to be expelled from the liquid chamber through the aperture; and a selecting mechanism disposed on the barrel that is actuated to select only one of the contents indicators.

In a preferred embodiment, the syringe has a selecting mechanism comprising a collar that is attached axially around the barrel. The collar in this preferred embodiment may further comprise a window portion through which a portion of the barrel may be viewed, and wherein the portion of the barrel viewed has associated therewith a selected one of the contents indicators. One or more unselected contents indicators associated with the barrel of the syringe may be obscured by the collar.

In another preferred embodiment, a proximal flange is disposed adjacent a proximal end of the barrel, the proximal flange having an aperture extending therethrough. The selecting mechanism includes a collar attached axially around the barrel and a proximally extending tab; and wherein the proximally extending tab extends into the aperture of the proximal flange and engages the proximal flange. The engagement of the proximally extending tab and the proximal flange acts to retain the collar in rotational engagement with the barrel.

The syringe may also be provided with a pair of finger flanges extending radially from a proximal flange disposed adjacent a proximal end of the barrel.

The syringe, may also include a supplemental identification portion associated with the selecting mechanism. This supplemental identification portion may be marked on with pen or may receive stickers or other information conveying indicia.

In an alternative embodiment, the syringe comprises a plunger; a barrel including a bore and a distal end having an aperture therethrough, the barrel having associated therewith two or more contents indicators, the barrel having further associated therewith a selecting mechanism that may be actuated such that the selecting mechanism identifies one of the contents indicators; and the barrel further comprising a locking tab capable of engaging a locking portion on the selecting mechanism, whereby the selecting mechanism may be locked in place after the appropriate contents indicator is identified.

In a further alternative embodiment, the syringe comprises a barrel including a bore and a distal end having an aperture therethrough, a plunger comprising two or more contents indicators printed on the proximal end of the plunger stem, the proximal end of the plunger having further associated therewith a selecting mechanism that may be actuated such that the selecting mechanism identifies one of the contents indicators.

These and other features of this invention are described in, or are apparent from, the following detailed description of various exemplary embodiments of this invention.

BRIEF DESCRIPTION OF THE DRAWINGS

Various exemplary embodiments of this invention will be described in detail, with reference to the following figures, wherein.

DETAILED DESCRIPTION OF THE PREFERRED EMBODIMENT

Figure 1:
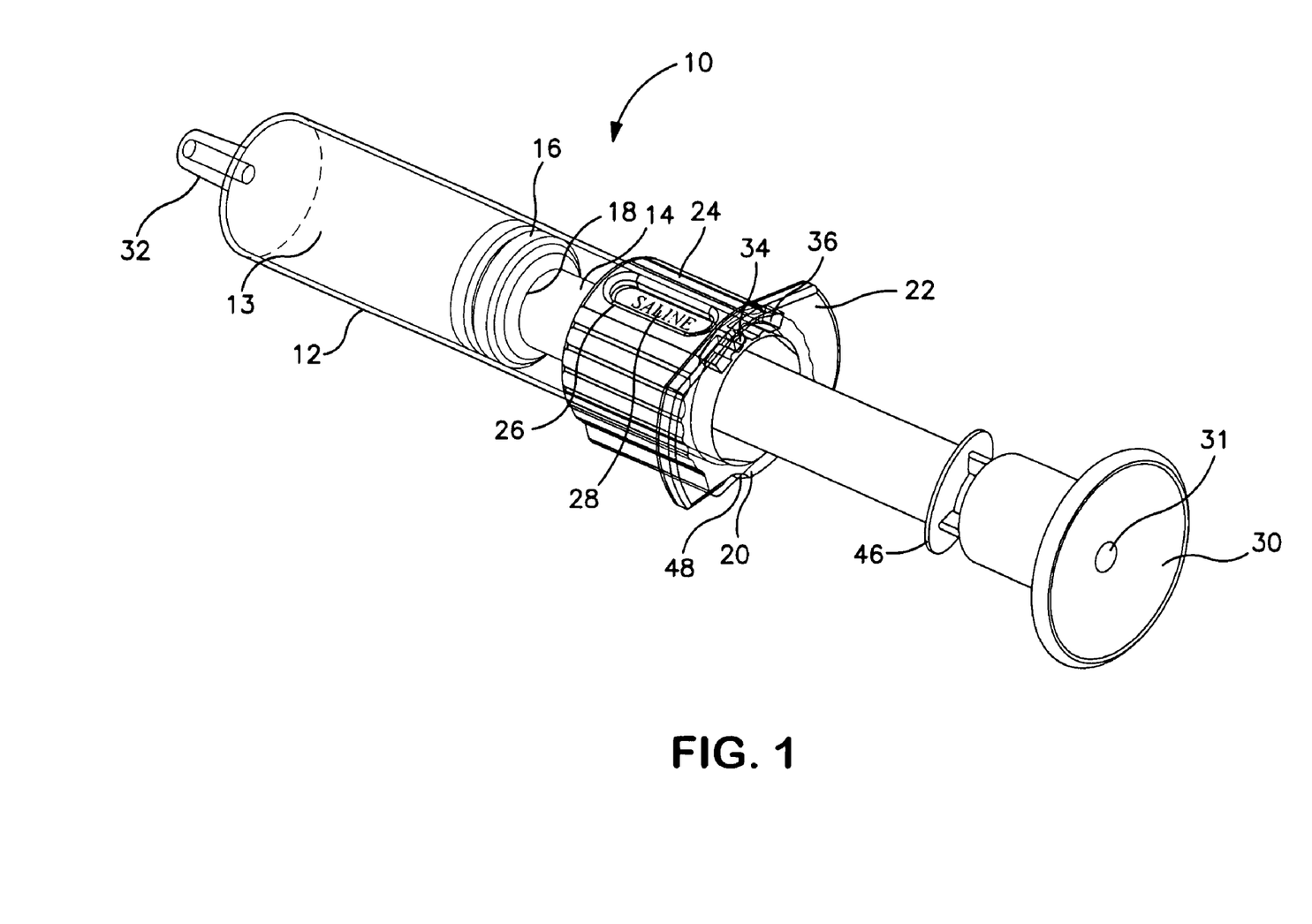
FIG. 1 is a partially transparent perspective view showing the plunger and internal features of a syringe barrel according to an exemplary embodiment of the present invention.
Figure 2:
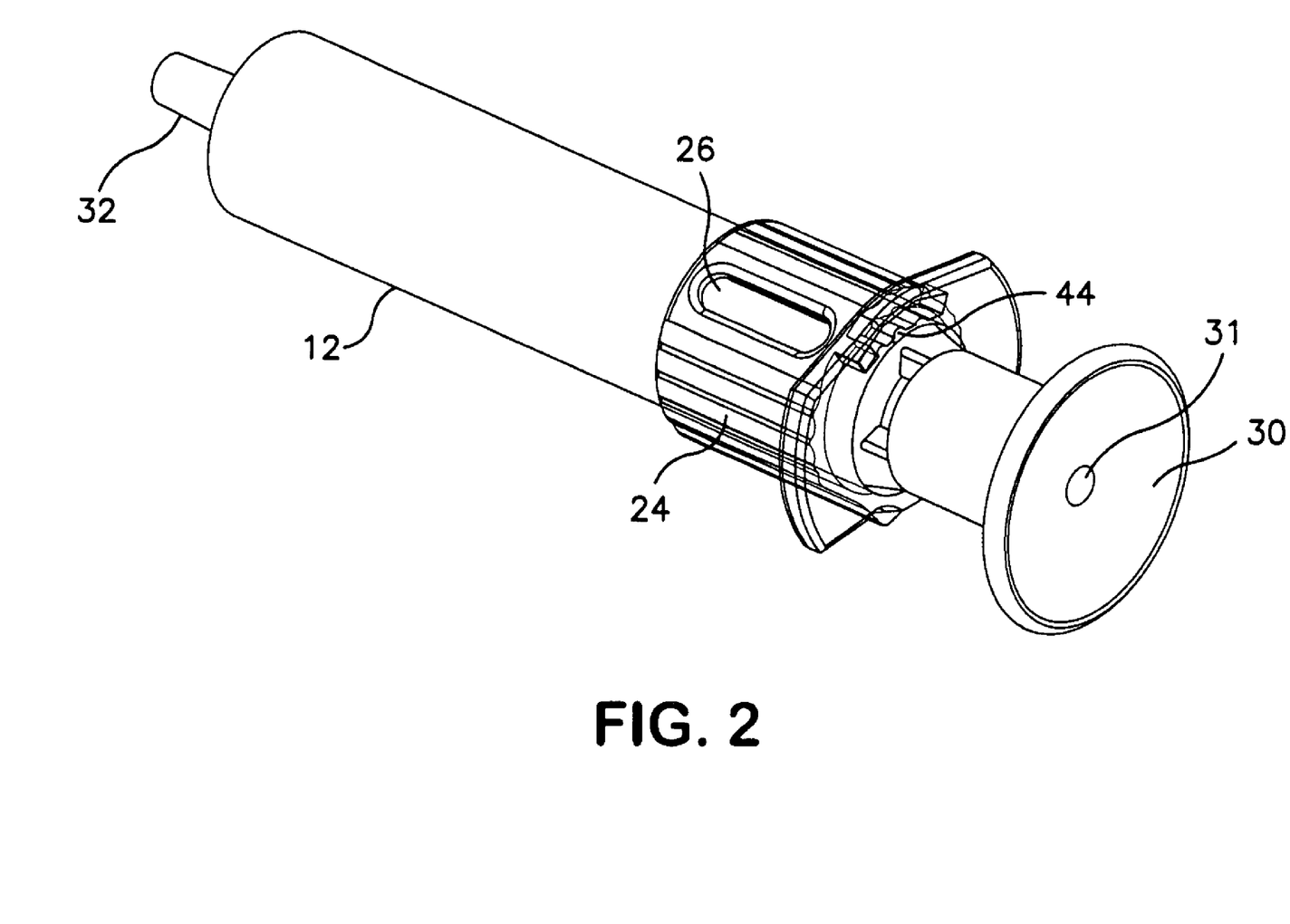
FIG. 2 is a partially transparent perspective view of the syringe of FIG. 1 showing the plunger inserted fully into the barrel.

FIG. 1 is a partially transparent perspective view of a syringe 10 according to an exemplary embodiment of the invention. The three basic components of syringe 10 are barrel 12, plunger 14 and contents indicator collar 24. Although portions of plunger 14 and internal features of barrel 12 are visible in FIG. 1, this does not necessarily mean that they would be visible in a physical embodiment of the syringe, i.e. structures of syringe 10 may be of a transparent material or of an opaque material.

Plunger 14 fits in the central bore 13 of barrel 12. A sealing element 16 is attached to the distal end portion 18 of plunger 14. Sealing element 16 comes into sliding/sealing contact with the cylindrical inner wall of barrel 12. The distal end of barrel 12, the cylindrical inner wall of barrel 12, and the sealing element 16 of plunger 14 define the portion of central bore 13 capable of containing a liquid to be delivered by the syringe 10. The size of the liquid containing portion of central bore 13 may be varied by the sliding displacement of plunger 14 relative to barrel 12. Thus, the liquid containing portion of central bore 13 can be varied in size from nearly the entire volume of central bore 13 to zero or nearly zero volume.

Syringe 10 may contain a great variety of liquids. With the distal end portion 16 of plunger 14 in contact with the distal end of barrel 12 or nearly so, the liquid port 32 may be put into contact with a liquid source; withdrawal of the plunger by way of handle 30 will cause a vacuum in central bore 13, thus causing liquid to fill the liquid containing portion of central bore 13 through liquid port 32. Liquid is prevented from entering the non-liquid containing portion of central bore 13, i.e. proximal of distal end portion 18, by the sealing contact between sealing element 16 of plunger 14 and the inner wall of barrel 12.

When it is desired to deliver the liquid contained in the liquid containing portion of syringe 10, handle 30 is compressed distally, causing plunger 14 to move distally and reduce the size of the liquid containing portion of central bore 13 thus creating a pressure that causes the liquid to exit liquid port 32. Finger wings 22 are provided at the end of barrel 12 to allow a practitioner to accomplish this compression of handle 30 with a thumb and two fingers disposed distally of wings 22 in the standard syringe manner.

The identity of the liquid contained in syringe 10 is often difficult or impossible to determine accurately using sensory perception. This being the case, the present invention provides a simple and accurate method of identifying the syringe contents. This identifying structure is both simple to use and requires a specific intent to change, such that alteration of this identification in an accidental manner is less likely.

Contents indicator collar 24, seen in FIGS. 1-4, includes a collar window 26. Collar 24 may be rotated circumferentially about barrel 12 but is prevented from axial displacement by interaction between retention tab 42 and barrel flange 20. As most clearly seen in FIG. 4, multiple contents indicator designations 28 may be printed on the external surface of barrel 12. Each of these contents indicator designations 28 is sized to be easily readable through collar window 26.

Circumferential rotation of collar 24 results in displacement of collar window 26 and registration thereof with a different contents indicator designation 28. Thus, a practitioner may fill the liquid containing portion of central bore 13 with a particular liquid, as described previously, and identify the contents of syringe 10 by rotating collar 28 such that collar window 26 is in registration with the appropriate contents indicator designation 28. Alternatively, a practitioner may identify the contents of syringe 10 by rotating collar 28 such that collar window 26 is in registration with the appropriate contents indicator designation 28 and then fill the liquid containing portion of central bore 13 with the designated liquid.

Selection tab 34 extends proximally from the proximal end of collar 24. Selection tab 34 extends into selection slot 36 which is formed in barrel flange 20 which extends axially from the proximal end of barrel 12. Selection slot 36 has disposed therein one or more selection cams 44. Selection cams 44 prevent circumferential movement of selection tab 34 in selection slot 36 absent a significant rotational force exerted on collar 24. In the absence of a significant rotational force, selection tab 34 will not displace relative to selection slot 36. As a result of the restraining action of the selection cams 44, collar 24 and collar window 26 cannot be easily accidentally displaced with respect to barrel 12. When a significant rotational force is exerted on collar 24, selection tab 34 may be caused to deflect and slide over a selection cam 44. Once selection tab 34 has passed over a selection cam 44 it resiliently deflects back to its original shape, again preventing collar 24 from circumferential rotation without significant rotational force being exerted. Placement of the selection cams 44 and the terminal ends of slot 36 are chosen such that an unstressed selection tab 34 position corresponds to collar window 26 being in registration with a single contents indicator designation 28.

Figure 3:
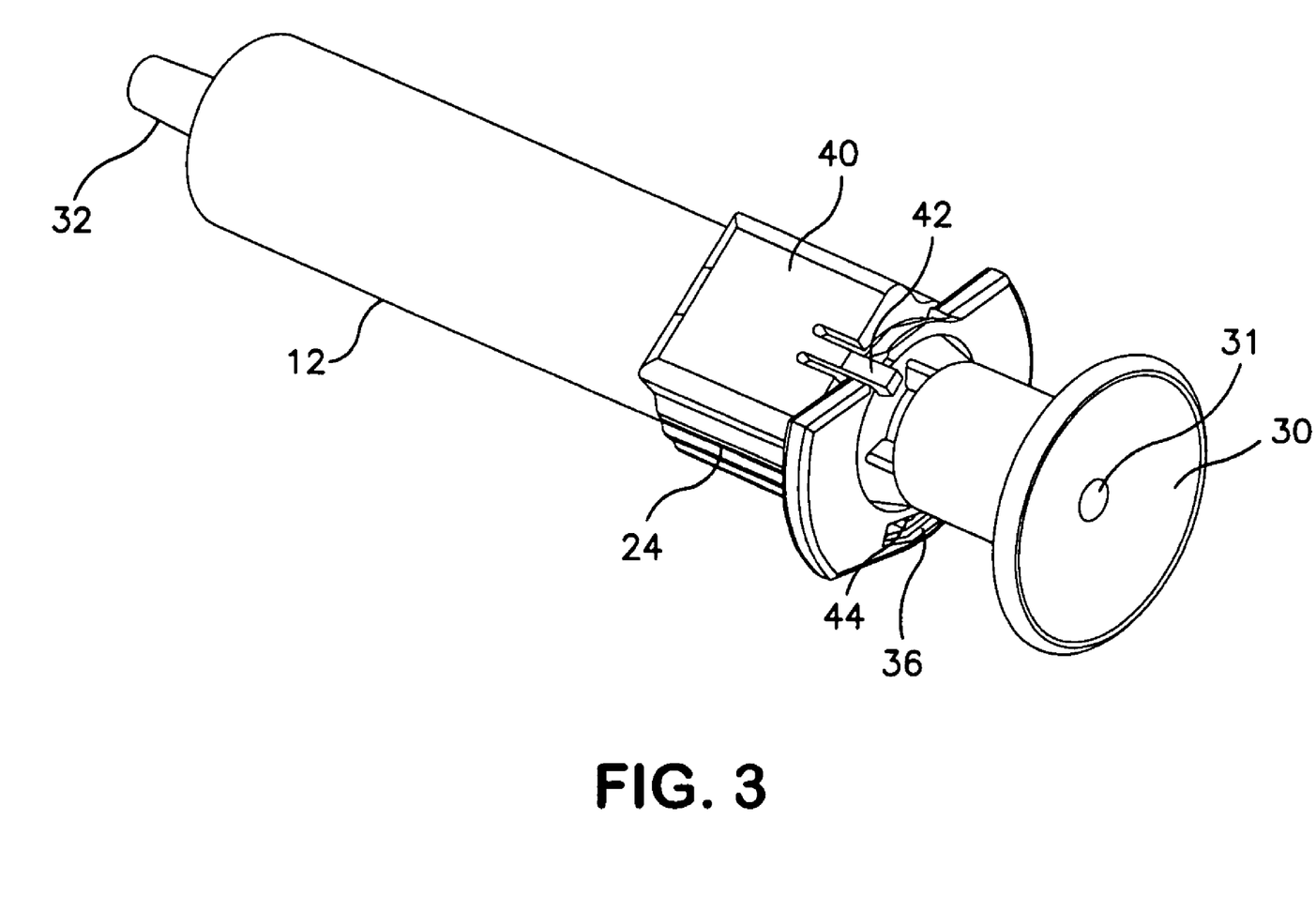
FIG. 3 is a bottom perspective view of the syringe of FIG. 1.
Figure 4:
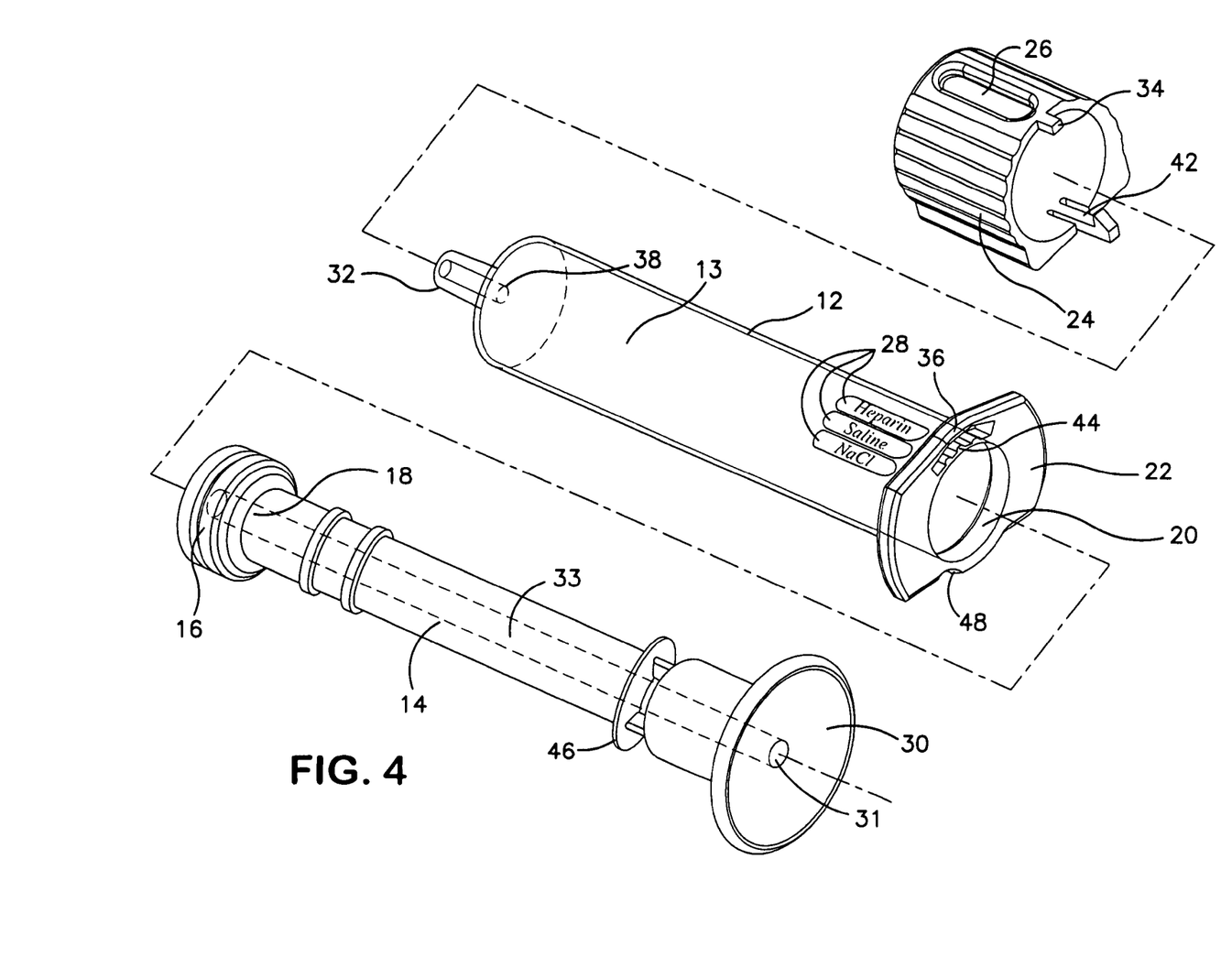
FIG. 4 is an exploded partially transparent perspective view of a syringe according to an exemplary embodiment of the present invention.

Retention tab 42, as best seen in FIGS. 3 and 4, performs a dual role. The first role of retention tab 42 is to prevent axial displacement of contents indicator collar 24, as discussed previously. The barrel flange 20 and plunger 14 may also be configured such that retention tab 42 prevents plunger 14 from being displaced proximally. Retention tab 42 engages plunger flange 46 when retention tab 42 is aligned with cut-out 48 in barrel flange 20, as shown in FIG. 3.

The retention tab 42, plunger flange 46, barrel flange 20, and cut-out 48 structures may be used as a reminder to the practitioner to use the indicia mechanism of the present invention. Thus, examples of an appropriate contents indicator designation 28 when retention tab 42 is aligned with cut-out 48 include no designation, i.e. contents indicator designation 28 is left blank, or the words "Choose Syringe Contents" or the like are used. Only upon rotation of collar 24 and selection of a contents indicator designation will barrel flange 20 deflect retention tab 42 such that retention tab 42 no longer engages plunger flange 46. Thus, collar 24 must be rotated before plunger 14 may be displaced proximally to fill syringe 10 with liquid. This requirement will increase the likelihood of the person filling the syringe first utilizing the contents indicia feature of the syringe of the present invention.

In an alternative embodiment of the present invention, one contents indicator designation 28 may read "Turn Over" or similar language. The contents identification area 40 is an area on the contents indicator collar 24 capable of receiving written or other indicia of syringe 10 contents. Contents identification area 40 may be capable of receiving ink from a pen or marker, or may be capable of having a sticker attached thereto. Contents identification area 40 may be used as a 'miscellaneous' indicator of syringe contents, i.e. where the syringe contents in not one of the available contents indicator designations 28. Contents identification area 40 may also be utilized in combination with an available contents indicator designation 28 to record, for example, the concentration of the solution contained in the syringe or the identity of the person who filled the syringe or the time when the syringe was filled. The use of stickers, preprinted or color coded, in conjunction with the contents identification area 40 is an alternative to written information especially where the use of a pen is difficult or inadvisable.

An alternative embodiment of the present invention is shown in FIGS. 5-8. This alternative embodiment seeks more positive and permanent locking of the contents indicator collar 24 once a contents indicator designation 28 has been chosen.

Figure 5:
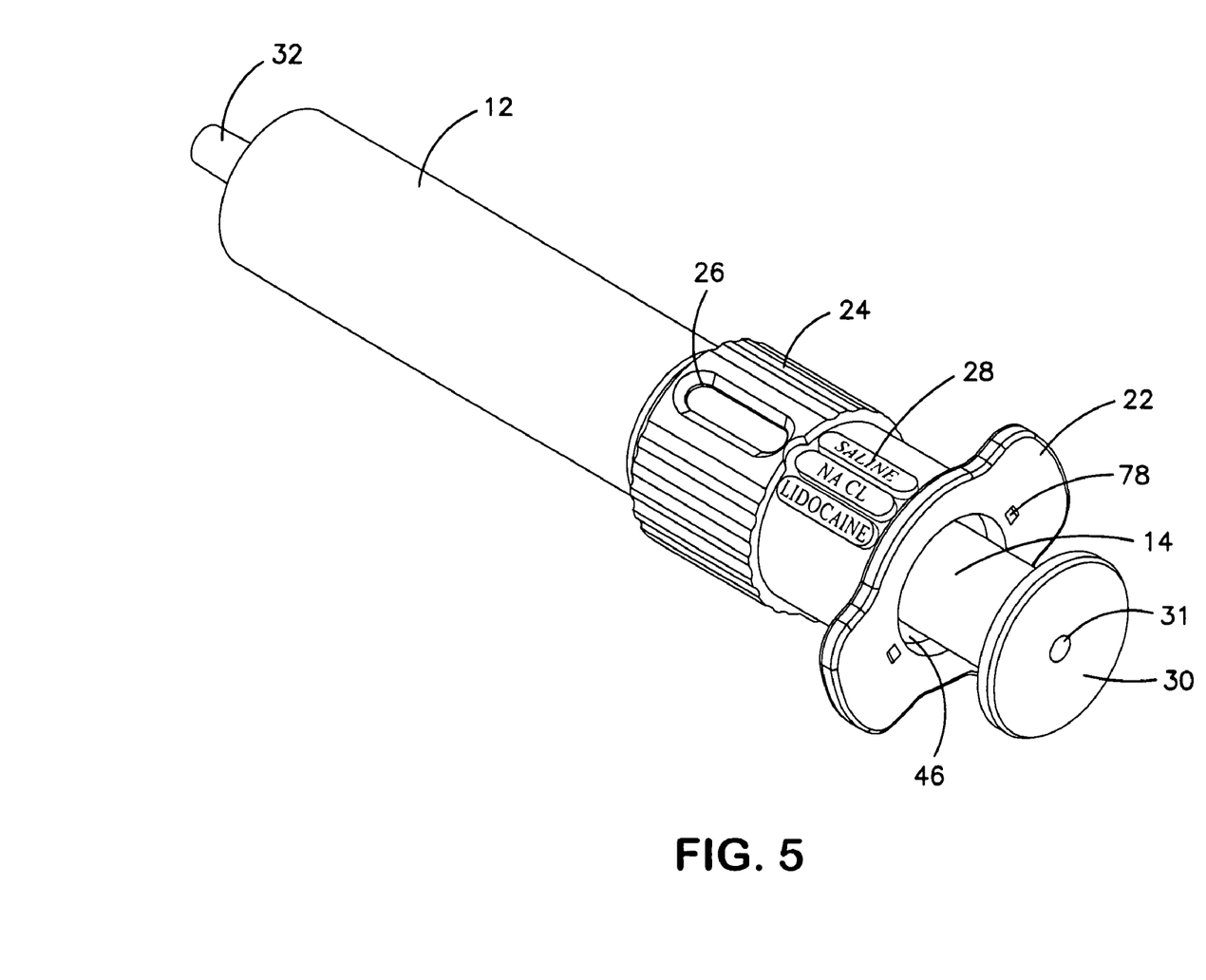
FIG. 5 is a perspective view showing of a syringe according to another exemplary embodiment of the present invention.
Figure 7:
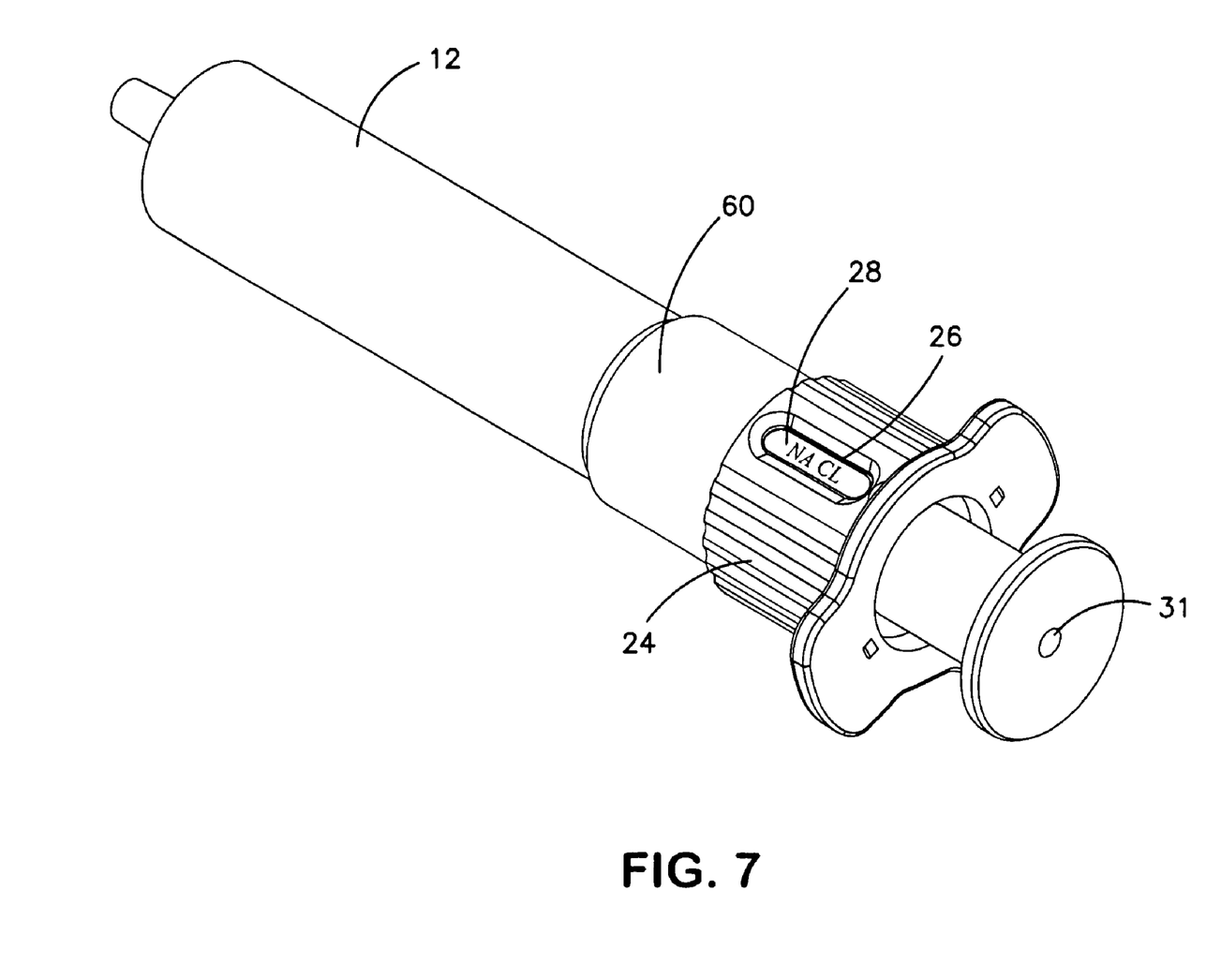
FIG. 7 is a perspective view of the syringe of FIG. 5 with the collar locked in place.

FIG. 5 illustrates the position of the contents indicator collar 24 when supplied to the medical professional, i.e. the collar 24 is disposed distally of the contents indicator designations 28. The practitioner chooses a contents indicator designation 28 utilizing the collar window 26. Once a contents indicator designation 28 is chosen, collar 24 may be slid axially along the barrel 12 of syringe 10 in the proximal direction. Once the collar 24 abuts the finger wings 22 and barrel flange 20, as seen in FIGS. 7, the collar 24 is locked in place and the appropriate contents indicator designation 28 appears in collar window 26.

In this alternative embodiment, collar 24 may not be moved, either axially or rotationally, once it is locked in place. This prevents inadvertent alteration of the contents indicator designation 28. In addition, collar 24 must be locked in place prior to filling the syringe 10. These functions are accomplished utilizing specialized structures associated with the contents indicator sleeve 60. A plurality of tab engagement grooves 74 are provided on the inside surface of collar 24. Each tab engagement groove 74 is indexed to a contents indicator designation 28. As will be further discussed below, locking tab 72 enters into the tab engagement groove 74 indexed to the contents indicator designation 28 chosen by the person filling the syringe 10.

Figures 8, 8A, 8B:
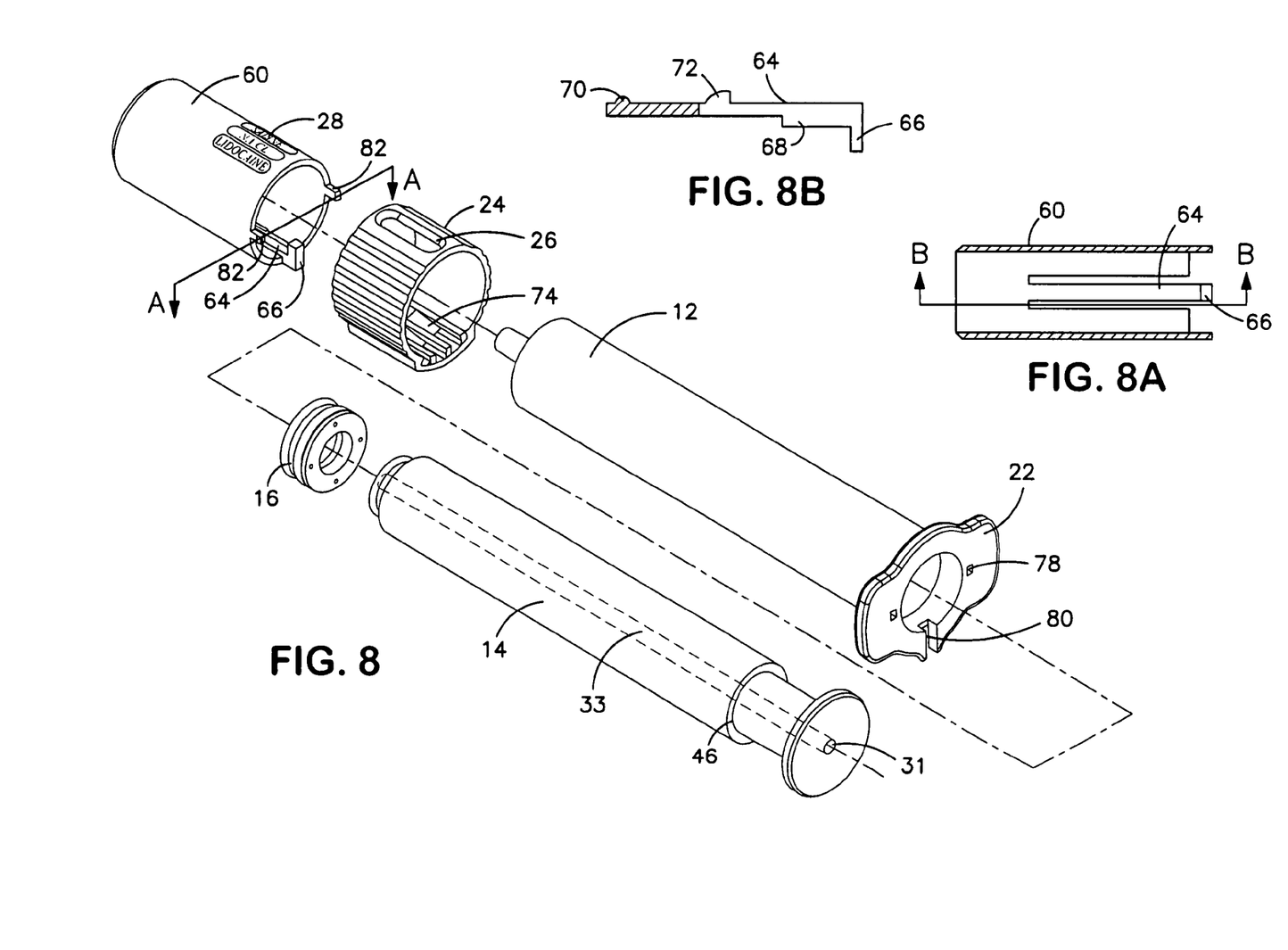
FIG. 8 is an exploded partially transparent perspective view of the syringe of FIG. 5.
FIG. 8A is a cross sectional view of contents indicator sleeve 60 taken along line A-A.
FIG. 8B is a cross sectional view of contents indicator sleeve 60 taken along line B-B.

Contents indicator sleeve 60 is disclosed in FIG. 8 and in two cross sections in FIGS. 8A and 8B. Contents indicator sleeve 60 fits over barrel 12 and is retained on barrel 12 through any standard engagement method such as adhesive, welding, interference fit or the like. Tabs 82 and holes 78 are utilized to assure proper alignment of indicator sleeve 60 and to assist in retention thereof on barrel 12.

Contents indicator sleeve 60 also has an arm 64. Arm 64 has several tabs along its length. At the extreme proximal end of arm 64 is plunger flange engagement tab 66, which extends through barrel flange notch 80 and engages plunger flange 46 and prevents withdrawal of plunger 14 from barrel 12. That is, plunger flange engagement tab 66 in its unstressed position, shown in FIG. 8, prevents filling of syringe 10 by engaging with plunger flange 46 and preventing movement of plunger 14.

Adjacent the distal end of contents indicator sleeve 60 on the arm 64 is retention tab 70. Retention tab 70 retains collar 24 on contents indicator sleeve 60, i.e. retention tab 70 prevents collar 24 from movement distally of the distal end of contents indicator sleeve 60. Retention tab 70 retains collar 24 by engaging a portion of tab engagement grooves 74 disposed on the inside surface of collar 24. Between plunger flange engagement tab 66 and retention tab 70 on the arm 64 is locking tab 72. Locking tab 72 locks collar 24 in place when the appropriate contents indicator designation has been chosen and the collar 24 has been moved proximally from the position shown in FIG. 5 to the position shown in FIG. 7, as discussed previously. Locking tab 72 interacts with tab engagement groove 74 on the inner surface of collar 24. The engagement between locking tab 72 and tab engagement groove 74 prevents any relative movement between collar 24 and contents indicator sleeve 60, whether axial or rotational. Thus, collar 24 is permanently locked into position once locking tab 72 engages tab engagement groove 74.

Figure 6:
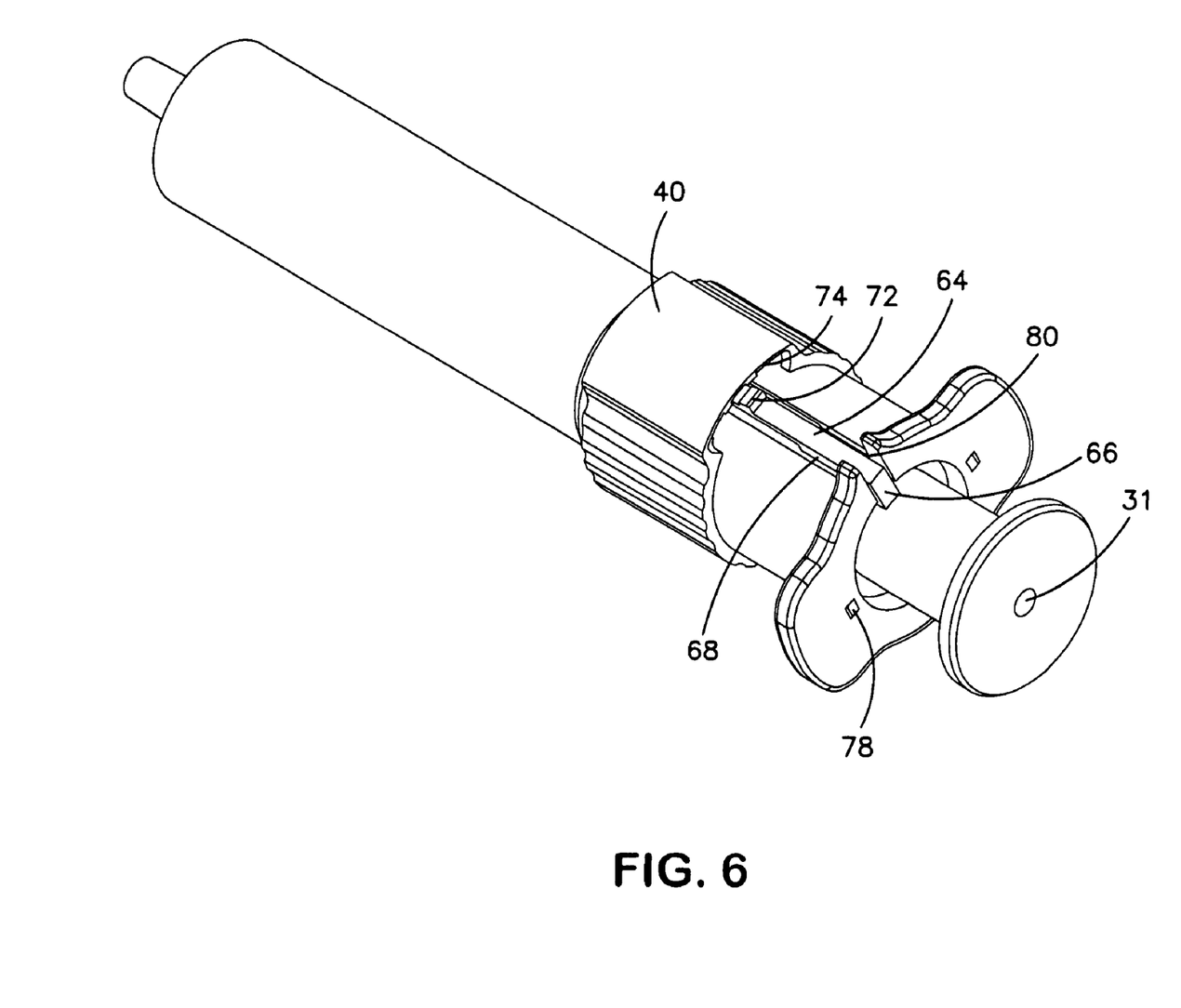
FIG. 6 is a perspective view showing the bottom of the syringe of FIG. 5.

Another function of locking tab 72 and tab engagement groove 74 is to cause the disengagement of plunger flange engagement tab 66 from plunger flange 46 and, thus, allow operation of the syringe 10. As seen in FIGS. 6 and 8, locking tab 72 is located between the ends of arm 64. Before the appropriate contents indicator designation 28 is chosen and collar 24 is slid proximally along indicator sleeve 60, plunger flange engagement tab prevents withdrawal of plunger 14 though blocking plunger flange 46. However, when collar 24 is moved proximally with respect to contents indicator sleeve 60, locking tab 72 enters one of several available tab engagement grooves 74, as shown in FIG. 6. Each tab engagement groove 74 is dimensioned such that a radial force is exerted on locking tab 72 as collar 24 is slid radially. The force on locking tab 72 and engagement of cantilever element 68 with the barrel 12 causes plunger flange engagement tab 66 to flex away from the plunger. This flexing of plunger flange engagement tab 66 causes it to cease blocking plunger flange 46, thus allowing displacement of plunger 14 with respect to barrel 12. Tab engagement groove 74 is dimensioned such that, even after locking tab 72 has locked collar 24 in position, a force remains on locking tab 72 such that plunger flange engagement tab 66 remains flexed away from plunger 14 such that it does not block plunger flange 46.

Figure 9:
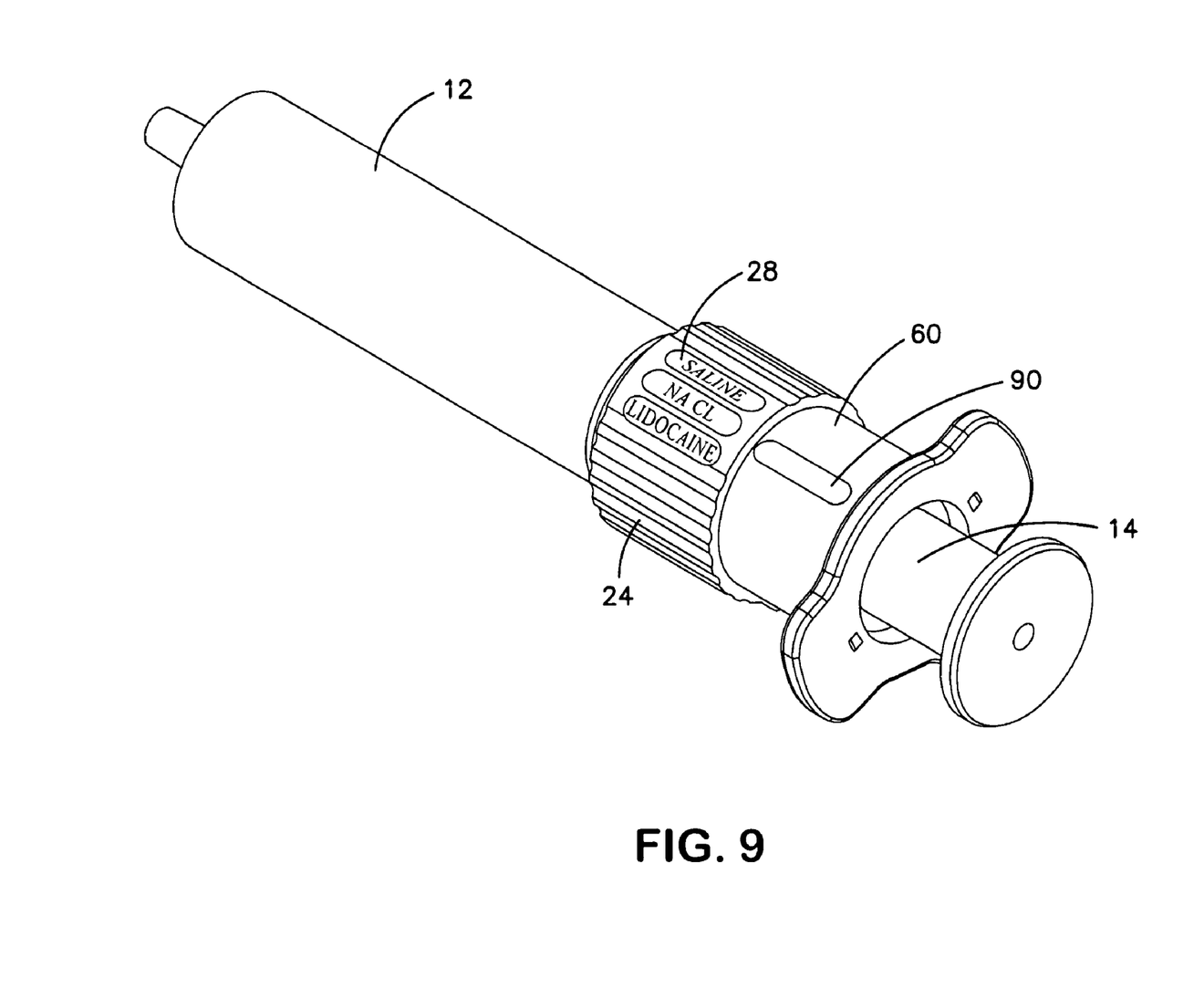
FIG. 9 is a perspective view showing a syringe according to another exemplary embodiment of the present invention.
Figure 10:
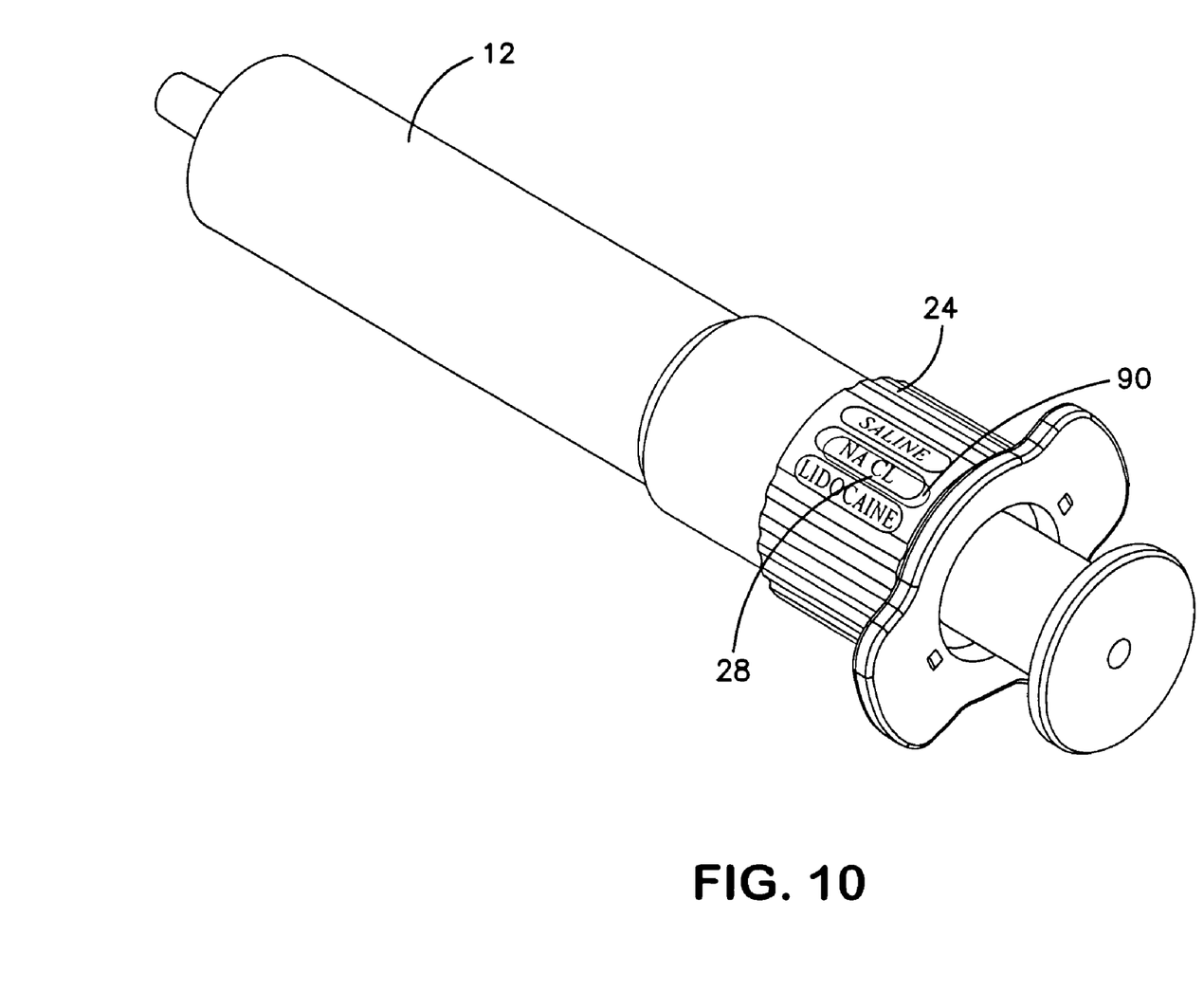
FIG. 10 is a perspective view of the syringe of FIG. 9 with the contents indicator collar locked in place.

FIGS. 9 and 10 show another exemplary embodiment of the present invention, in which collar 24 may be supplied with contents indicator designations 28 on the surface thereof. A contrasting background 90 may be printed on the barrel 12 or on the contents indicator sleeve 60. In this embodiment, collar 24 must be at least partially transparent. When the appropriate contents indicator designation 28 is indexed with the contrasting background 90, taking the place of the contents indicator window 26, the chosen contents indicator designation 28 is shown in a contrasting relationship to the non-chosen contents indicators.

Figure 11:
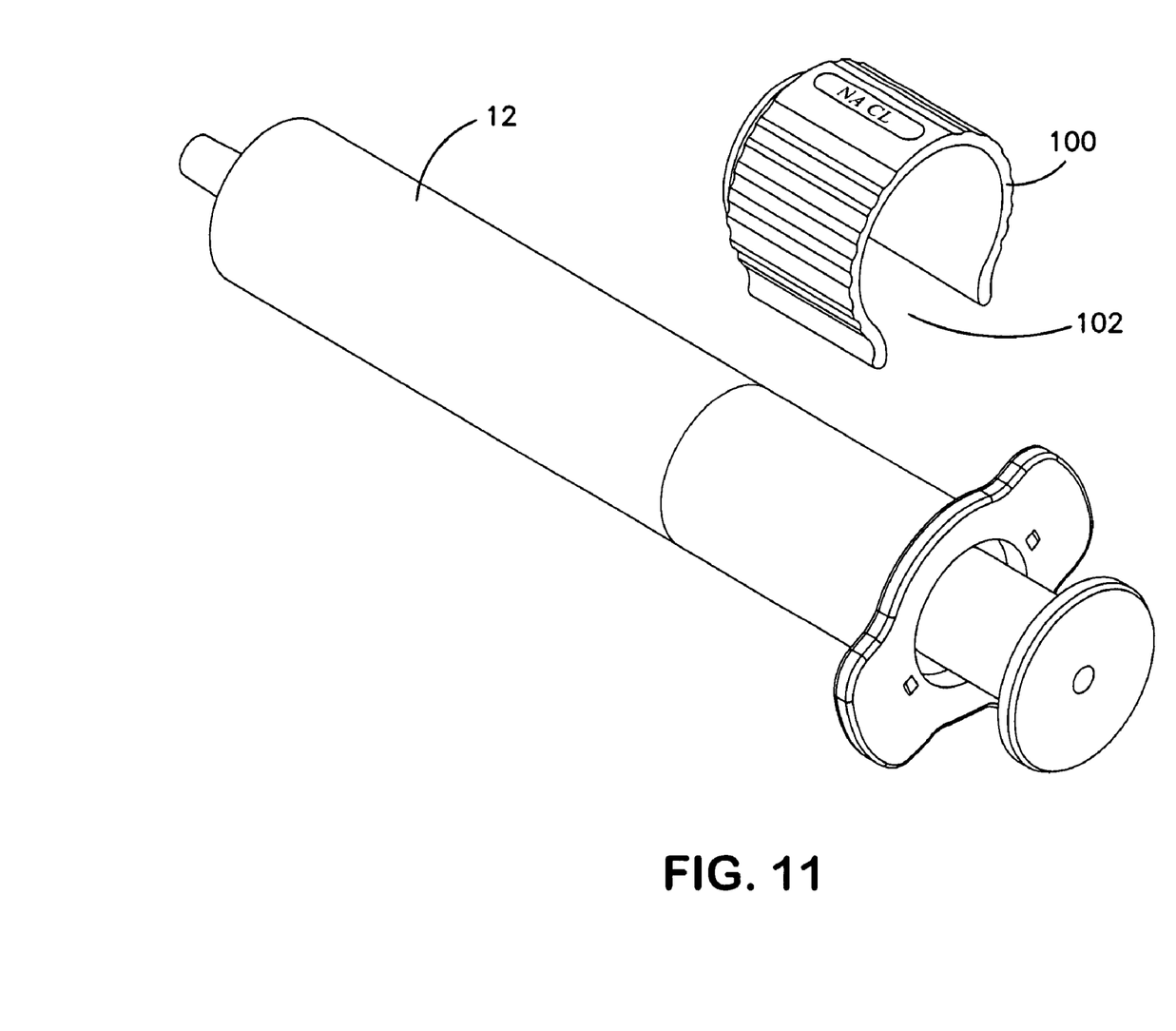
FIG. 11 is a perspective view of a syringe according to another exemplary embodiment of the present invention with the contents indicator structure removed from the syringe barrel.
Figure 12:
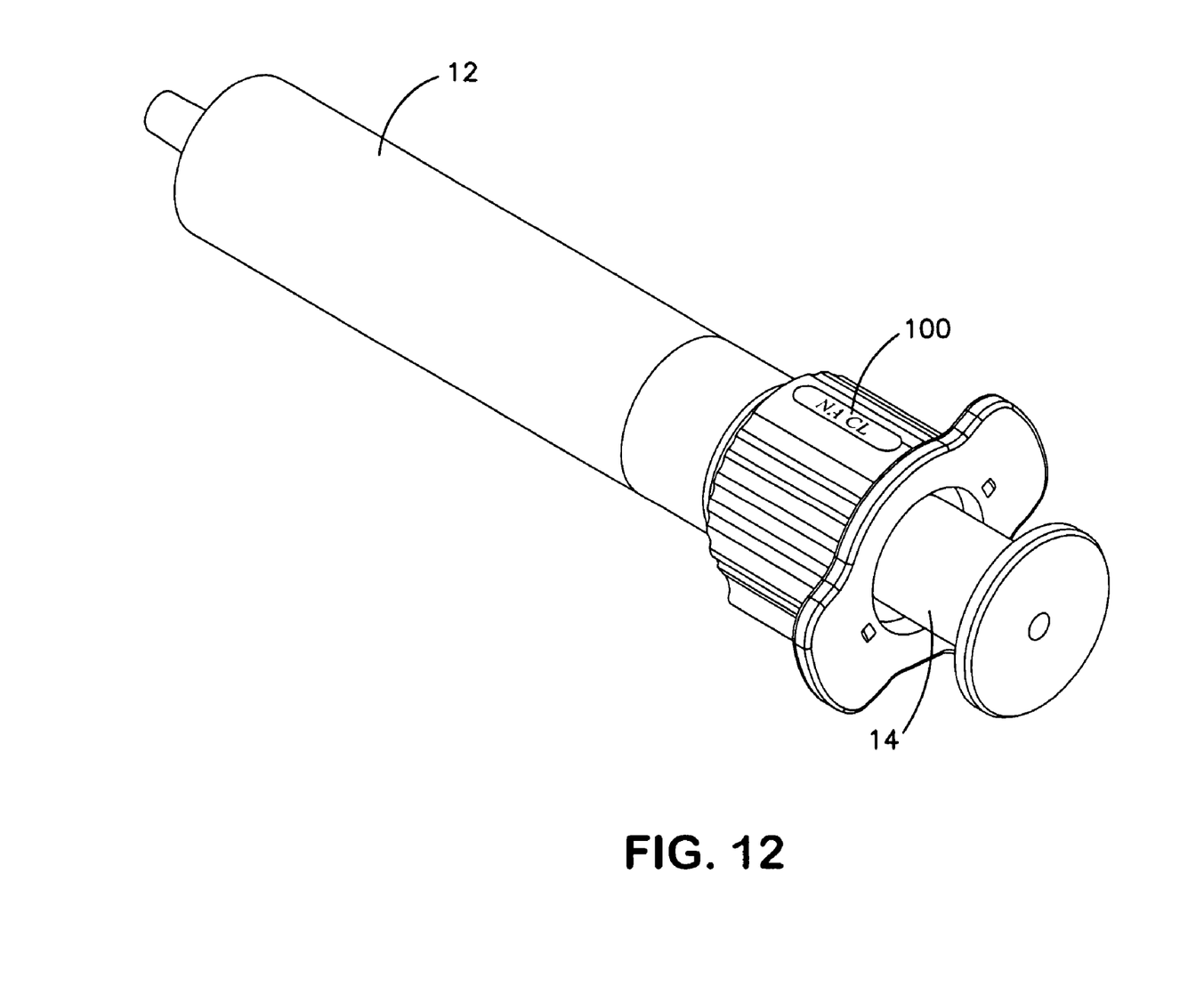
FIG. 12 is a perspective view of the syringe of FIG. 11 with the contents indicator collar disposed over the syringe barrel.

Another exemplary embodiment of the present invention is disclosed in FIGS. 11 and 12. In this embodiment, instead of providing multiple contents indicator designations 28 associated with the barrel or contents indicator sleeve, a selection of preprinted contents indicator collars 100 is provided. Each preprinted collar 100 has an opening 102 allowing the preprinted collar 100 to be snapped over barrel 12. This embodiment may be used with either specialized syringes 10 or with generic syringes. Different sizes of preprinted collars, each size capable of being preprinted with a large assortment of contents indicators, may be sold to accommodate most syringe sizes.

Another feature that may be utilized with any of the contents indicator syringes-described herein is the ability to provide guidewire access. As most completely disclosed in FIGS. 4 and 8, a bore 33 may be formed along the entire length of plunger 14. This bore 33 extents from an entrance point 31, through the entire length of the plunger 31, and then through distal end portion 18 and sliding element 16 of plunger 14. This bore 33 may be used to feed a guidewire through the syringe 10; syringe 10 provides access to the patient for a guidewire (not shown).

Figure 13:
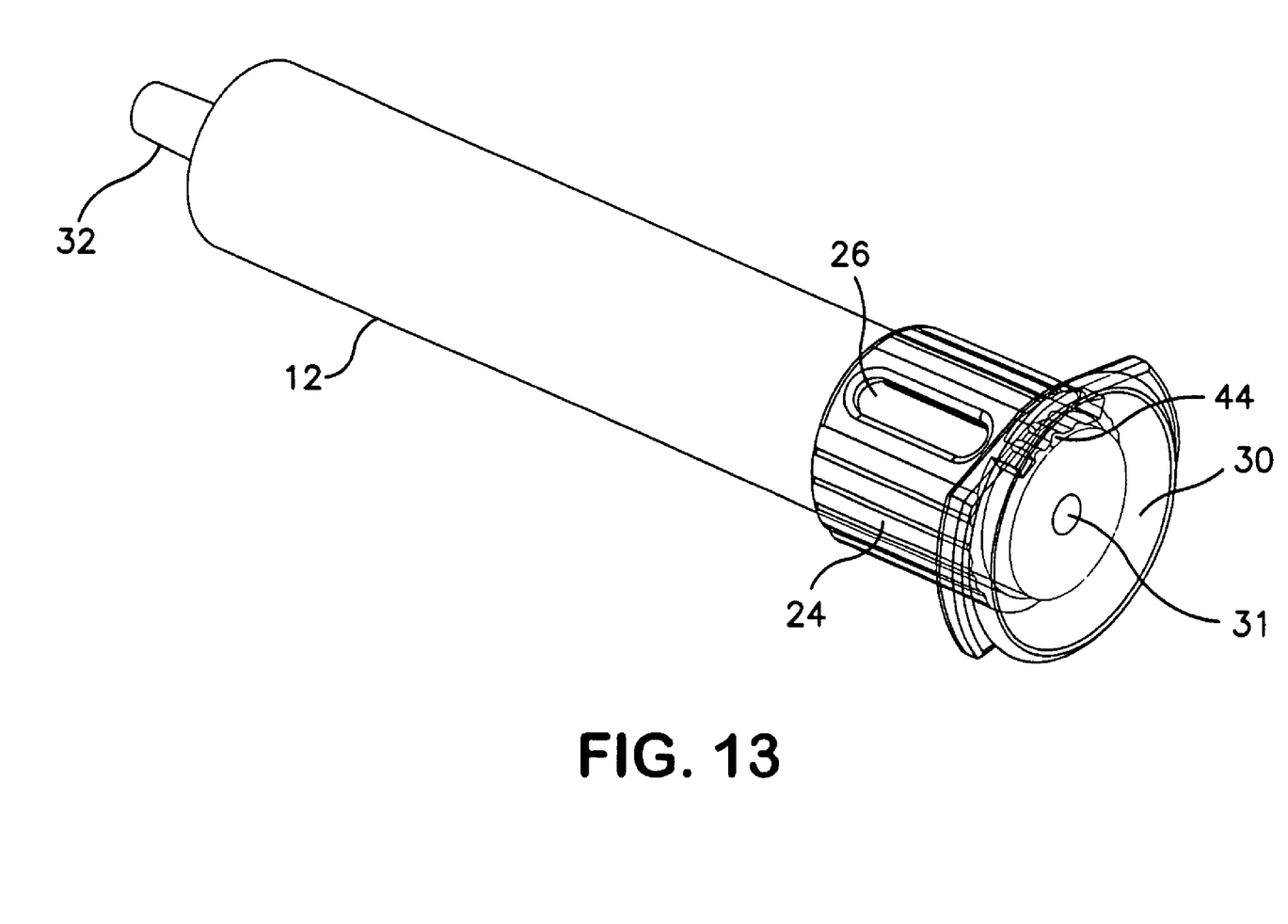
FIG. 13 is a perspective view of a syringe according to another exemplary embodiment of the present invention.

FIG. 13 discloses an alternative structure for syringe 10. Collar 24 may also circumferentially engage plunger 14. In this alternative embodiment, contents indicator designations 28 are associated with the cylindrical surface adjacent the proximal end of plunger 14. Collar 24 engages plunger 14 in such a way that window 26 may be rotated to overlie one of contents indicator designations 28. Selection slot 36 is located in handle 30 of plunger 14. Selection tab 34 extends from the proximal end of collar 24 and engages selection cams 44 in selection slot 36. These elements operate in the same manner as discussed previously.

In its most general structure, the contents indicator takes the form of any actuatable structural element that may be actuated from one position to another in order to select one of a plurality of contents indicator designations. Examples have been provided above but are not limiting. Other non-limiting examples include: (i) an axially sliding contents indicator that can be actuated to select one of a plurality of contents indicator designations; (ii) an arrow like contents indicator that can be actuated to select one of a plurality of contents indicator designations; and (iii) a set of actuatable shutters that can be actuated to obscure the non-selected contents indicator designations, leaving only the selected one of the plurality of contents indicators viewable.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A syringe comprising:
    a barrel defining a liquid chamber, an aperture and two or more contents indicators;
    a plunger movable within said barrel whereby movement of the plunger in a first direction causes the liquid chamber to fill with a fluid and movement by the plunger in a second direction causes fluid to be expelled from the liquid chamber through the aperture; and
    a selecting mechanism disposed on the barrel that is actuated to select only one of the two or more contents indicators; and further comprising
    a proximal flange disposed at a proximal end of the barrel, the proximal flange having an aperture extending therethrough;
    the selecting mechanism including a collar attached axially around the barrel and a proximally extending tab; and
    wherein the proximally extending tab extends into the aperture of the proximal flange and engages a plunger flange, the engagement of the proximally extending tab and the plunger flange acting to retain the plunger from axial movement relative to the barrel and further wherein rotation of the selecting mechanism results in disengagement of the proximally extending tab from the aperture and the plunger flange.

2. The syringe of claim 1, wherein the selecting mechanism comprises a collar that is attached axially around the barrel.

3. The syringe of claim 2, wherein the collar further comprises a window portion through which a portion of the barrel may be viewed, and wherein the portion of the barrel viewed has the selected one of the contents indicators.

4. The syringe of claim 3, further wherein one or more unselected contents indicators are obscured by the collar.

5. The syringe of claim 1, further comprising a pair of finger flanges extending radially from a proximal flange disposed adjacent a proximal end of the barrel.

6. The syringe of claim 1, wherein the selecting mechanism comprises a collar that is rotationally attached axially around the barrel, the collar including a window portion through which a portion of the barrel may be viewed, and wherein the portion of the barrel viewed has associated therewith the selected one of the contents indicators.

7. The syringe of claim 6, wherein the collar covers the contents indicators not aligned with the window portion.

8. The syringe of claim 1, further including a supplemental identification portion associated with the selecting mechanism.

9. The syringe of claim 8, wherein the supplemental identification portion comprises an area capable of receiving one of markings from a pen or marker and stickers conveying contents information.

10. The syringe of claim 1, wherein the selecting mechanism comprises a collar that is rotationally attached axially around the barrel and at least a portion of which is at least partially transparent, the collar having printed thereon a plurality of contents indicators and further wherein a contrasting portion of the barrel can be caused, in at least one configuration, to underlie only one contents indicator.

11. A syringe comprising:
    a barrel defining a liquid chamber, an aperture and two or more contents indicators;
    a plunger movable within said barrel whereby movement of the plunger in a first direction causes the liquid chamber to fill with a fluid and movement by the plunger in a second direction causes fluid to be expelled from the liquid chamber through the aperture; and
    a selecting mechanism disposed on the barrel that is actuated to select only one of the two or more contents indicators,
    wherein the plunger comprises a plunger flange, and the selecting mechanism further comprises a locking tab in locking engagement with the plunger flange, the locking tab and plunger flange engagement preventing proximal axial movement of the plunger prior to selection of one of the contents indicators by the selecting mechanism.

12. The syringe of claim 11, wherein the selecting mechanism comprises a collar that is attached axially around the barrel.

13. The syringe of claim 12, wherein the collar further comprises a window portion through which a portion of the barrel may be viewed, and wherein the portion of the barrel viewed has the selected one of the contents indicators.

14. The syringe of claim 13, further wherein one or more unselected contents indicators are obscured by the collar.

15. The syringe of claim 11, further comprising a pair of finger flanges extending radially from a proximal flange disposed adjacent a proximal end of the barrel.

16. The syringe of claim 11, wherein the selecting mechanism comprises a collar that is rotationally attached axially around the barrel, the collar including a window portion through which a portion of the barrel may be viewed, and wherein the portion of the barrel viewed has associated therewith the selected one of the contents indicators.

17. The syringe of claim 16, wherein the collar covers the contents indicators not aligned with the window portion.

18. The syringe of claim 11, further including a supplemental identification portion associated with the selecting mechanism.

19. The syringe of claim 18, wherein the supplemental identification portion comprises an area capable of receiving one of markings from a pen or marker and stickers conveying contents information.

20. The syringe of claim 11, wherein the selecting mechanism comprises a collar that is rotationally attached axially around the barrel and at least a portion of which is at least partially transparent, the collar having printed thereon a plurality of contents indicators and further wherein a contrasting portion of the barrel can be caused, in at least one configuration, to underlie only one contents indicator.

21. A syringe comprising:
a barrel including a bore and a distal end having an aperture therethrough, the barrel having associated therewith two or more contents indicators, the barrel having further associated therewith a selecting mechanism that is actuated to select only one of the contents indicators; and
a plunger movable within the barrel; and further comprising
a sleeve coaxially overlying the barrel having a locking mechanism, the locking mechanism capable of locking an engagement structure on the selecting mechanism whereby the selecting mechanism is locked in place once a selection is made,
wherein the plunger comprises a plunger flange, and the selecting mechanism further comprises a locking tab in locking engagement with the plunger flange, the locking tab and plunger flange engagement preventing axial movement of the plunger prior to identification of one of the contents indicators by the selecting mechanism.

22. The syringe of claim 21, wherein the selecting mechanism comprises a collar that is attached axially around the barrel.

23. The syringe of claim 22, wherein the collar further comprises a window portion through which a portion of the barrel may be viewed, and wherein the portion of the barrel viewed has associated therewith the selected one of the contents indicators.

24. The syringe of claim 23, a further wherein one or more unselected contents indicators associated with the barrel of the syringe is obscured by the collar.

* * * * *